United States Patent
Johnson et al.

(10) Patent No.: US 9,044,243 B2
(45) Date of Patent: Jun. 2, 2015

(54) SURGICAL CUTTING AND FASTENING DEVICE WITH DESCENDIBLE SECOND TRIGGER ARRANGEMENT

(75) Inventors: Gregory W. Johnson, Milford, OH (US); Jeffrey S. Swayze, Hamilton, OH (US); Jason L. Harris, Mason, OH (US); Foster B. Stulen, Mason, OH (US); Prasanna Malaviya, Mason, OH (US)

(73) Assignee: Ethcon Endo-Surgery, Inc., Cincinnati, OH (US)

( * ) Notice: Subject to any disclaimer, the term of this patent is extended or adjusted under 35 U.S.C. 154(b) by 874 days.

(21) Appl. No.: 13/221,410

(22) Filed: Aug. 30, 2011

(65) Prior Publication Data

US 2013/0053831 A1 Feb. 28, 2013

(51) Int. Cl.
*A61B 18/12* (2006.01)
*A61B 18/14* (2006.01)
*A61B 17/29* (2006.01)
(Continued)

(52) U.S. Cl.
CPC ......... *A61B 18/1445* (2013.01); *A61B 17/2909* (2013.01); *A61B 2017/2912* (2013.01); *A61B 2017/2923* (2013.01); *A61B 2017/2925* (2013.01); *A61B 2018/00619* (2013.01); *A61B 2018/1455* (2013.01); *A61B 2017/0042* (2013.01)

(58) Field of Classification Search
CPC ........... A61B 17/2909; A61B 18/1445; A61B 2017/2912; A61B 2017/2923; A61B 2017/2925; A61B 2018/1455

USPC .................................. 606/27, 34, 41, 48–52
See application file for complete search history.

(56) References Cited

U.S. PATENT DOCUMENTS

| 2,366,274 A | 1/1945 | Luth et al. |
| 2,458,152 A | 1/1949 | Eakins |
| 2,510,693 A | 6/1950 | Green |

(Continued)

FOREIGN PATENT DOCUMENTS

| DE | 29623113 U1 | 10/1997 |
| DE | 20004812 U1 | 9/2000 |

(Continued)

OTHER PUBLICATIONS

International Search Report for PCT/US2012/051686, Jan. 24, 2013 (5 pages).

(Continued)

*Primary Examiner* — Michael Peffley
*Assistant Examiner* — Daniel Fowler

(57) ABSTRACT

A nested trigger assembly for a surgical instrument may generally comprise a first trigger and a second trigger, wherein the first trigger and the second trigger are movable together on a first stroke of the nested trigger assembly, wherein the second trigger is configured to be biased away from the first trigger after the first stroke and before a second stroke, and wherein the second trigger is configured to be moved toward to the first trigger during the second stroke. A surgical instrument may generally comprise a shaft comprising a proximal end and a distal end, a handle extending from the proximal end, wherein the handle comprises a gripping portion, and a nested trigger assembly extending from the handle. The nested trigger assemble may comprise one of a separable trigger assembly and a divisible trigger assembly.

20 Claims, 8 Drawing Sheets

(51) Int. Cl.
 *A61B 18/00* (2006.01)
 *A61B 17/00* (2006.01)

(56) References Cited

U.S. PATENT DOCUMENTS

| | | |
|---|---|---|
| 3,166,971 A | 1/1965 | Stoecker |
| 3,580,841 A | 5/1971 | Cadotte et al. |
| 3,703,651 A | 11/1972 | Blowers |
| 4,005,714 A | 2/1977 | Hiltebrandt |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,545,926 A | 10/1985 | Fouts, Jr. et al. |
| 4,550,870 A | 11/1985 | Krumme et al. |
| 4,582,236 A | 4/1986 | Hirose |
| 4,761,871 A | 8/1988 | O'Connor et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,190,541 A | 3/1993 | Abele et al. |
| 5,205,459 A | 4/1993 | Brinkerhoff et al. |
| 5,285,945 A | 2/1994 | Brinkerhoff et al. |
| 5,309,927 A | 5/1994 | Welch |
| 5,318,589 A | 6/1994 | Lichtman |
| 5,387,207 A | 2/1995 | Dyer et al. |
| 5,389,098 A | 2/1995 | Tsuruta et al. |
| 5,395,312 A | 3/1995 | Desai |
| 5,403,312 A | 4/1995 | Yates et al. |
| 5,428,504 A | 6/1995 | Bhatla |
| 5,465,895 A * | 11/1995 | Knodel et al. ............... 227/176.1 |
| 5,480,409 A * | 1/1996 | Riza ............................. 606/205 |
| 5,496,317 A | 3/1996 | Goble et al. |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,618,307 A | 4/1997 | Donlon et al. |
| 5,624,452 A | 4/1997 | Yates |
| 5,647,871 A | 7/1997 | Levine et al. |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,876,401 A | 3/1999 | Schulze et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,483 A | 8/2000 | Palmer et al. |
| 6,099,550 A | 8/2000 | Yoon |
| H1904 H | 10/2000 | Yates et al. |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B1 | 12/2002 | Truckai et al. |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,055,731 B2 | 6/2006 | Shelton, IV et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,252,667 B2 | 8/2007 | Moses et al. |
| 7,267,685 B2 | 9/2007 | Butaric et al. |
| 7,287,682 B1 | 10/2007 | Ezzat et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,491,201 B2 | 2/2009 | Shields et al. |
| 7,510,107 B2 | 3/2009 | Timm et al. |

(56) References Cited

U.S. PATENT DOCUMENTS

| | | |
|---|---|---|
| 7,513,025 B2 | 4/2009 | Fischer |
| 7,517,349 B2 | 4/2009 | Truckai et al. |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,645,277 B2 | 1/2010 | McClurken et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,981,113 B2 | 7/2011 | Truckai et al. |
| 8,020,743 B2 | 9/2011 | Shelton, IV |
| 8,070,036 B1 | 12/2011 | Knodel et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 | 8/2012 | Bucciaglia et al. |
| 8,282,669 B2 | 10/2012 | Gerber et al. |
| 8,298,232 B2 | 10/2012 | Unger |
| 8,323,310 B2 | 12/2012 | Kingsley |
| 2002/0165541 A1 | 11/2002 | Whitman |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0085809 A1 | 4/2005 | Mucko et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173813 A1 | 7/2007 | Odom |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0269862 A1* | 10/2008 | Elmouelhi et al. ............ 607/122 |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0138003 A1 | 5/2009 | Deville et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0320268 A1 | 12/2009 | Cunningham et al. |
| 2009/0326530 A1 | 12/2009 | Orban, III et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0087208 A1 | 4/2011 | Boudreaux et al. |
| 2011/0087209 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0190809 A1* | 8/2011 | Mohan et al. ............... 606/205 |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251612 A1 | 10/2011 | Faller et al. |
| 2011/0251613 A1 | 10/2011 | Guerra et al. |
| 2011/0264093 A1 | 10/2011 | Schall |
| 2011/0276057 A1 | 11/2011 | Conlon et al. |
| 2011/0282339 A1 | 11/2011 | Weizman et al. |
| 2011/0301605 A1 | 12/2011 | Horner |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306972 A1 | 12/2011 | Widenhouse et al. |
| 2011/0306973 A1 | 12/2011 | Cummings et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0101488 A1 | 4/2012 | Aldridge et al. |

(56) References Cited

U.S. PATENT DOCUMENTS

| | | | |
|---|---|---|---|
| 2012/0136353 A1 | 5/2012 | Romero | |
| 2012/0150176 A1 | 6/2012 | Weizman | |
| 2013/0023875 A1 | 1/2013 | Harris et al. | |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/089717 A1 | 7/2011 |

OTHER PUBLICATIONS

Written Opinion for PCT/US2012/051686, Jan. 24, 2013 (6 pages).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

Wright, et al., "Time-Temperature Equivalence of Heat-Induced Changes in Cells and Proteins," Feb. 1998. ASME Journal of Biomechanical Engineering, vol. 120, pp. 22-26.

* cited by examiner

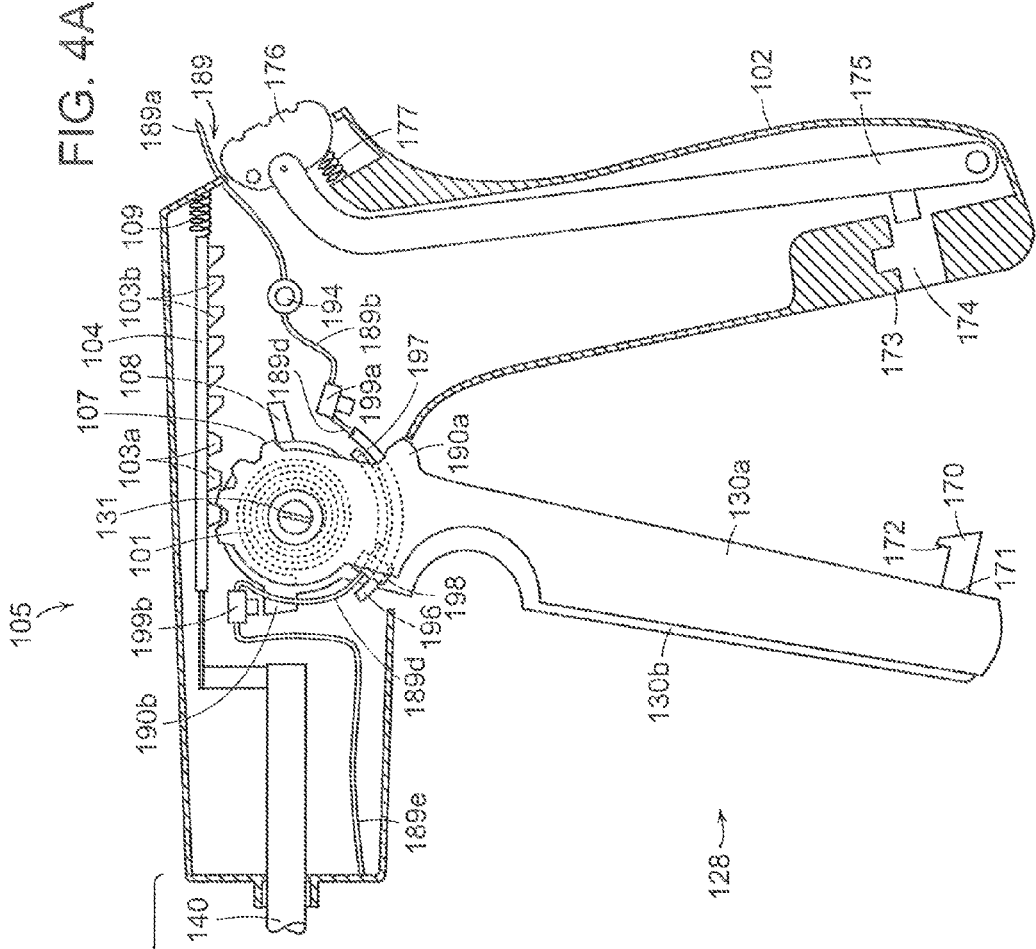
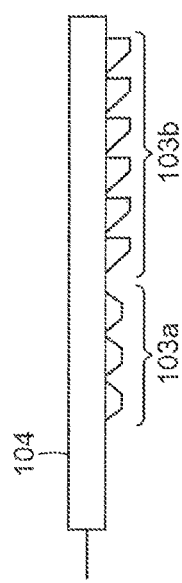
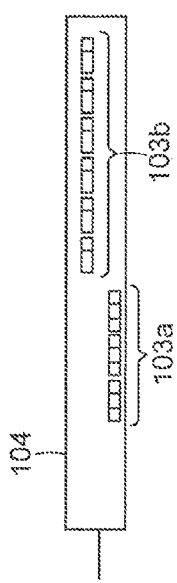

SURGICAL CUTTING AND FASTENING DEVICE WITH DESCENDIBLE SECOND TRIGGER ARRANGEMENT

BACKGROUND

1. Field of the Invention

The present invention generally relates to medical devices and methods, and in particular, surgical instruments configured to weld and/or incise tissue.

2. Description of the Related Art

In various open, endoscopic, and/or laparoscopic surgeries, for example, it may be necessary to coagulate, seal, and/or fuse tissue. One means of sealing tissue relies upon the application of electrical energy to tissue captured within an end effector of a surgical instrument in order to cause thermal effects within the tissue. Various mono-polar and bi-polar radio frequency (Rf) surgical instruments and surgical techniques have been developed for such purposes. In general, the delivery of Rf energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

In certain arrangements of a bi-polar radiofrequency surgical instrument, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate various aspects of the related art in the field of the invention at the time, and should not be taken as a disavowal of claim scope.

SUMMARY

In various embodiments, a surgical instrument may generally comprise a shaft comprising a proximal end and a distal end, a handle extending from the proximal end, wherein the handle comprises a gripping portion, and a divisible trigger assembly extending from the handle, wherein a portion of the divisible trigger assembly is movable relative to the gripping portion between an unactuated position, a first actuated position, a second actuated position, and a third actuated position. The divisible trigger assembly may generally comprise a first trigger portion and a second trigger portion, wherein the first trigger portion and the second trigger portion form a single component when the portion of the divisible trigger assembly is in the unactuated position, wherein the second trigger portion is released from the first trigger portion when the portion of the divisible trigger assembly is in the first actuated position, wherein the second trigger portion is spaced distally from the first trigger portion when the portion of the divisible trigger assembly is in the second actuated position, and wherein the second trigger portion and the first trigger portion again form the single component when the portion of the divisible trigger assembly is in the third actuated position.

In various embodiments, a separable trigger assembly for a surgical instrument may generally comprise a first trigger and a second trigger, wherein the first trigger and the second trigger are movable together on a first stroke of the separable trigger assembly, wherein the second trigger is configured to be biased away from the first trigger after the first stroke and before a second stroke, and wherein the second trigger is configured to be moved toward to the first trigger during the second stroke.

In various embodiments, a surgical instrument may generally comprise a shaft comprising a proximal end and a distal end, a handle extending from the proximal end, wherein the handle comprises a gripping portion, and a separable trigger assembly extending from the handle. The separable trigger assembly may generally comprise a first trigger movable between a first position distal from the gripping portion and a second position proximal to the gripping portion and a second trigger, wherein the second trigger forms part of the first trigger when the first trigger is in the first position, wherein the second trigger is configured to release from the first trigger when the first trigger is in the second position, and wherein the second trigger is movable toward the gripping portion once again after the second trigger has released from the first trigger.

The foregoing discussion should not be taken as a disavowal of claim scope.

BRIEF DESCRIPTION OF THE FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 4A is a cross-sectional view of a surgical device comprising a nested trigger assembly in an unactuated position according to various embodiments.

FIG. 4B is a cross-sectional view of a gear rack of a surgical device illustrated in FIG. 4A according to various embodiments.

FIG. 4C is a bottom view of the gear rack of FIG. 4B according to various embodiments.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
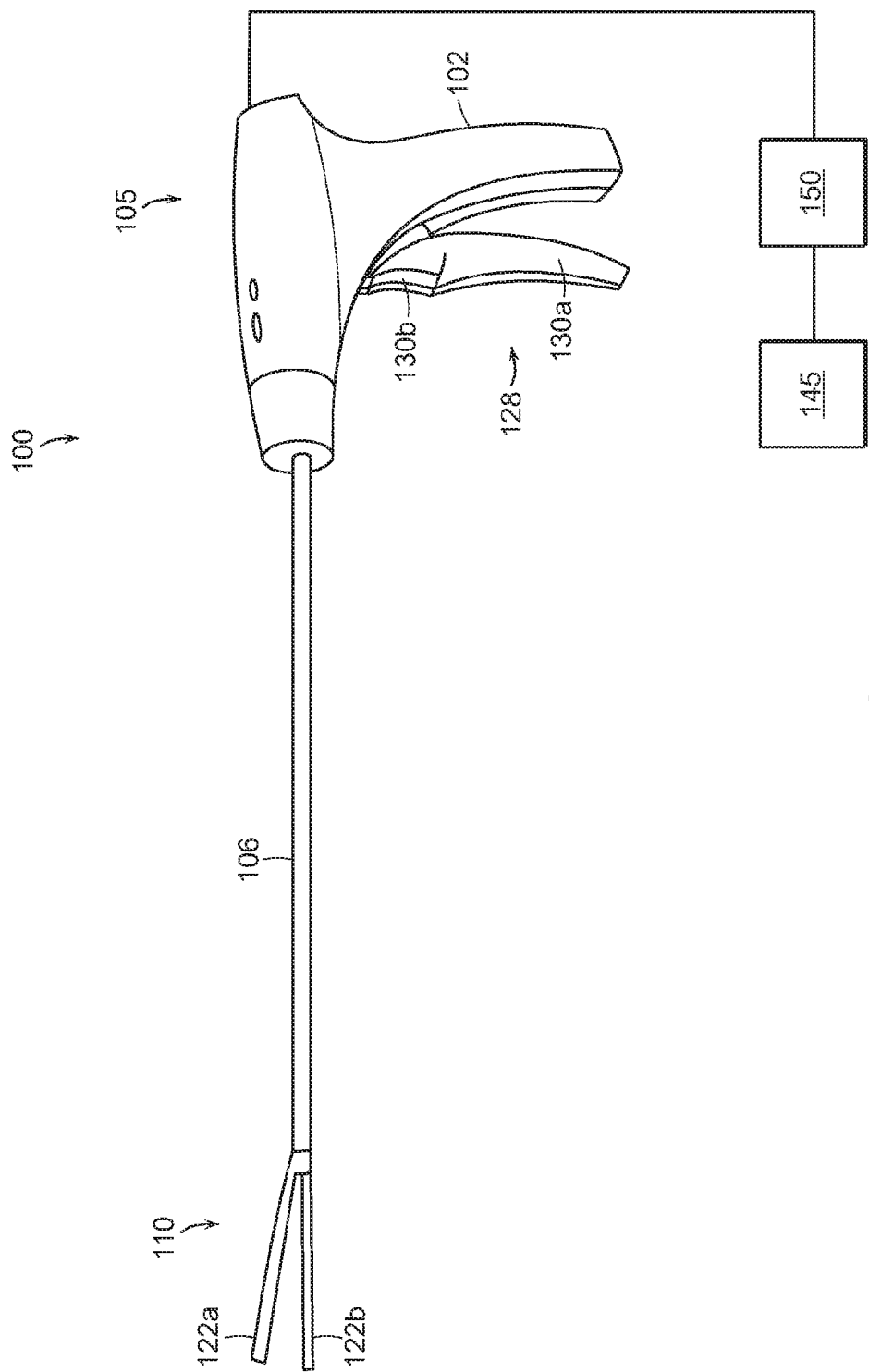
FIG. 1 is a perspective view of a surgical device comprising a nested trigger assembly according to various embodiments.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Various embodiments of systems and methods of the invention relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

Various embodiments disclosed herein provide electrosurgical jaw structures adapted for transecting captured tissue between the jaws and for contemporaneously welding the captured tissue margins with controlled application of Rf energy. The jaw structures can comprise a cutting element which can cut or score tissue independently of the tissue capturing and welding functions of the jaw structures. In various embodiments, as described in greater detail further below, the jaw structures can comprise first and second opposing jaws that carry positive temperature coefficient (PTC) bodies for modulating Rf energy delivery to the engaged tissue.

According to certain embodiments, as described in greater detail below, a nested trigger assembly for a surgical instrument may generally comprise one of a separable trigger assembly and a divisible trigger assembly. A nested trigger assembly may comprise a first trigger and a second trigger wherein the second trigger may form a portion of the first trigger prior to a first stroke of the nested trigger assembly. The first trigger and the second trigger may be movable together on a first stroke of the nested trigger assembly. The second trigger may be configured to be biased away from the first trigger after the first stroke and before a second stroke. In at least one such embodiment, the second trigger may be configured to release from the first trigger after the first stroke. Thereafter, the second trigger can be movable through a second stroke independently of the first trigger. During and/or after the second stroke, the second trigger may reform the nested trigger assembly with the first trigger.

In various embodiments, as described in greater detail further below, the surgical instrument may comprise an end-effector extending from the distal end of the shaft. The end effector may comprise an openable and closeable jaw assembly, and a knife edge as described herein. The end-effector may be configured to perform a first function and a second function. The first trigger may be configured to actuate the first function. In various embodiments, the first function may comprise opening and closing the jaw assembly. The first trigger may comprise a closure trigger configured to open and close the jaw assembly. The second trigger may be configured to actuate the second function. In various embodiments, the second function may comprise transecting tissue in the jaw assembly with the knife edge. The second trigger may comprise a firing trigger configured to move the knife edge distally to transect the tissue between the jaw assembly.

Referring now to an exemplary embodiment, FIG. 1 illustrates a surgical instrument 100 comprising a handle 105, a shaft or introducer 106, and an end effector or working end 110. The shaft 106 may comprise any suitable cross-section, such as, for example, a cylindrical cross-section and/or rectangular cross-section. In at least one embodiment, the shaft 106 may comprise a tubular sleeve that extends from the handle 105. In at least one such embodiment, a proximal end of the shaft 106 may be attached to the handle 105. In various embodiments, the handle 105 may comprise a gripping portion 102 and a nested trigger assembly, or lever arm, 128 extending from the handle 105. In various embodiments, as shown in FIG. 1, the nested trigger assembly 128 may comprise a divisible trigger assembly wherein, as described in greater detail below, the trigger assembly 128 may comprise a first trigger portion 130a and a second trigger portion 130b.

Further to the above, the end effector 110 of the surgical instrument 100 may extend from a distal end of the shaft 106. In various embodiments, the end effector 110 may be configured for clamping, transecting, and/or welding tissue, as described in greater detail further below; however, the end effector 110 may be suitable for various types of surgical devices, such as, for example, endocutters, graspers, cutters, staplers, clip appliers, access devices, drug/gene therapy devices, ultrasound devices, RF and/or laser devices. In various embodiments, further to the above, the end effector 110 may comprise a first jaw 122a, a second jaw 122b, and at least one electrode. In at least one such embodiment, the first jaw 122a may be movable relative to the second jaw 122b between an open position and a closed position. In use, the at least one electrode may be adapted to be activated to apply electrosurgical energy to weld tissue captured within the end effector 110 wherein the at least one electrode may be coupled to a radiofrequency (Rf) energy source.

Figure 2A:
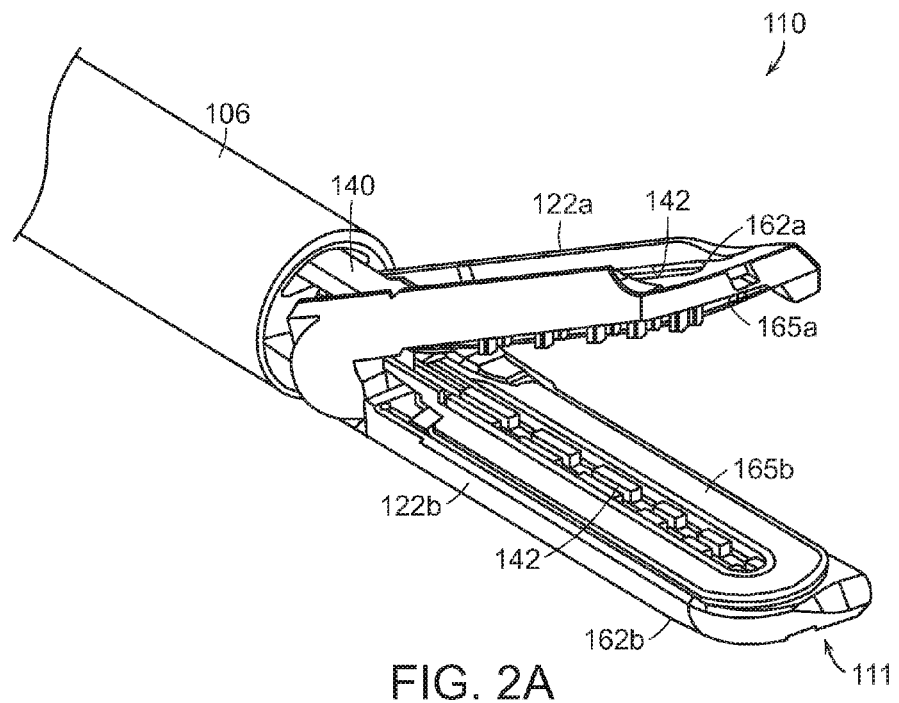
FIG. 2A includes an end effector of a surgical device in an open configuration according to various embodiments.

Referring to FIGS. 2A and B, in various embodiments, the end effector 110 may comprise at least openable and closeable jaw assembly comprising straight, curved, and/or any other suitably configured jaws. In at least one embodiment, the first jaw 122a may be pivoted about an axis relative to the second jaw 122b to close onto, capture, and/or engage tissue positioned between the jaws 122a and 122b. The jaws 122a and 122b may also apply a compression force or pressure thereto. In various embodiments, the first jaw 122a and second jaw 122b may each comprise a first positive temperature coefficient (PTC) body portion and a second positive temperature coefficient (PTC) body portion, respectively.

Figure 2B:
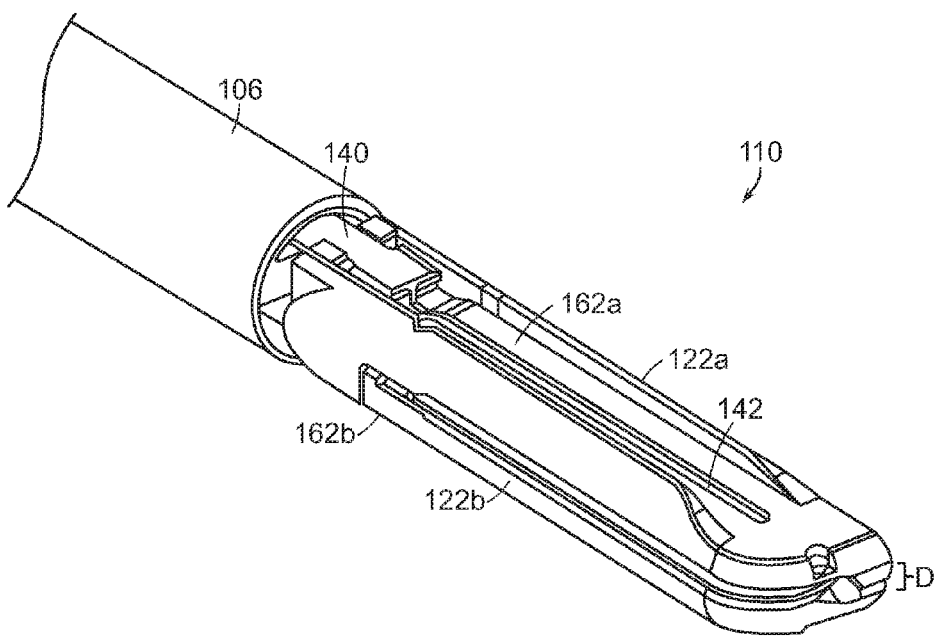
FIG. 2B includes the end effector of a surgical device in a closed configuration according to various embodiments.

Further to the above, the end effector 110 may comprise a translatable member 140 configured to contact first jaw 122a and pivot it downwardly toward second jaw 122b, as shown in FIG. 2B. In various embodiments, as described in greater detail below, the trigger assembly 128 may be configured to actuate the translatable member 140. In at least one such embodiment, each of the jaws 122a and 122b may comprise an elongate channel 142 disposed outwardly along their respective middle portions wherein the translatable member 140 may slide within channels 142 to open and close the first jaw 122a and/or the second jaw 122b. The distal end of translatable member 140 may comprise a flanged "I"-beam configured to slide within the channels 142 in the jaws 122a and 122b. The I-beam may comprise an upper flange, a lower flange, and a center, or intermediate, portion therebetween. In at least one embodiment, the flanges and the center portion may define "c"-shaped channels on the opposite sides of the translatable member 140. The flanges may define inner cam surfaces for slidably engaging outward-facing surfaces 162a and 162b of the jaws 122a and 122b, respectively. More particularly, a first inner cam surface may comprise any suitable profile configured to slidably engage the outer surface 162a of the first jaw 122a, and a second inner cam surface may comprise any suitable profile configured to slidably engage the outer surface 162b of the second jaw 122b such that, as translatable member 140 is advanced distally, the cam surfaces may co-operate to cam the first jaw 122a toward the second jaw 122b, and configure the end effector 140 in a closed configuration. As seen in FIG. 2B, the jaws 122a and 122b may define a gap, or dimension, D between a first electrode 165a of the first jaw 122a and a second electrode 165b of the second jaw when they are positioned in a closed configuration. In various embodiments, dimension D may equal a distance between approximately 0.0005 inches and approximately 0.005 inches, for example, and, in at least one embodiment, between approximately 0.001 inches and approximately 0.002 inches, for example.

In various embodiments, the translatable member 140 may be at least partially advanced toward the distal end 111 of the end effector 110 to move the first jaw 122a toward the second jaw 122b. Thereafter, the translatable member 140 may be advanced further toward the distal end 111 of the end effector 110 to transect the tissue positioned between the jaws 122a and 122b. In certain embodiments, the distal, or leading, end of the I-beam portion may comprise a sharp, or knife, edge 161 which may be configured to incise the tissue. Before, during, and/or after the translatable member 140 is advanced through the tissue, an electrical current may be supplied to the first electrode 165a and the second electrode 165bs to weld the tissue. In various embodiments, the operation of the trigger assembly 128, such as, for example, the second trigger portion 130b, may advance the knife edge 161 to the distal end of a slot or channel 142. After the knife edge 161 has been sufficiently advanced, the trigger assembly 128 may be released and moved to its original, or unactuated, position in order to retract the knife edge 161 and/or translatable member 140, and allow the first jaw 122a to move into its open position again. In at least one embodiment, the surgical instrument may comprise a jaw spring (not shown) configured to bias the first jaw 122a into its open position and/or a trigger spring, such as trigger spring 101, for example, configured to bias the trigger assembly 128 into its unactuated position. Various other jaw closing mechanisms and electrosurgical energy-delivery surfaces are described in the following United States patents, the entire disclosures of which are incorporated herein by reference: U.S. Pat. Nos. 7,220,951; 7,189,233; 7,186,253; 7,125,409; 7,112,201; 7,087,054; 7,083,619; 7,070,597; 7,041,102; 7,011,657; 6,929,644; 6,926,716; 6,905,497; 6,802,843; 6,770,072; 6,656,177; 6,533,784; and 6,500,176.

In various embodiments, the surgical instrument 100 may comprise a first conductor, such as, for example, an insulated wire, that may be operably coupled with the first electrode 165a in the first jaw 122a, and a second conductor, such as, for example, an insulated wire, that may be operably coupled with the second electrode 165b in the second jaw 122b. The first and second conductors may extend through shaft 106 between an electrical connector in the handle 105 and the first electrode 165a and second electrode 165b in the end effector 110. In use, the first and second conductors may be operably coupled to an electrical source 145 and a controller 150 by electrical leads in the cable 152 for the first electrode 165a and second electrode 165b to function as paired bi-polar electrodes with a positive polarity (+) and a negative polarity (−), for example. In at least one embodiment, one of the first electrode 165a and second electrodes 165b may be operably coupled with a positive (+) voltage terminal of the electrical source 145 and the other of the first electrode 165a and second electrode 165b may be electrically coupled with the negative voltage (−) terminal of the electrical source 145. Owing to the opposite polarities of the first electrode 165a and second electrode 165b, current may flow through the tissue positioned between the first electrode 165a and second electrode 165b and heat the tissue to a desired temperature. In certain embodiments, the translatable member 140 may act as an electrode when it is electrically coupled to a positive terminal or negative terminal of the electrical source 145, and/or any suitable ground.

Figure 3A:
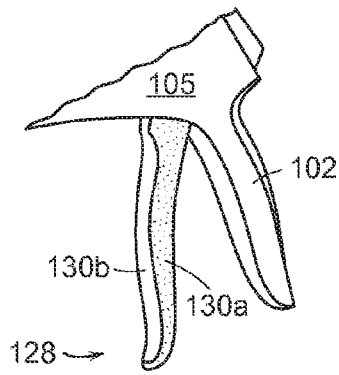
FIGS. 3A-F include a surgical device comprising a nested trigger assembly in various positions according to various embodiments.
Figure 3B:
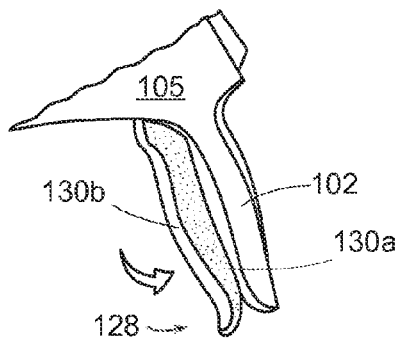
Figure 3C:
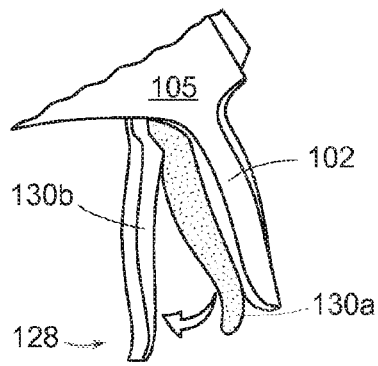
Figure 3D:
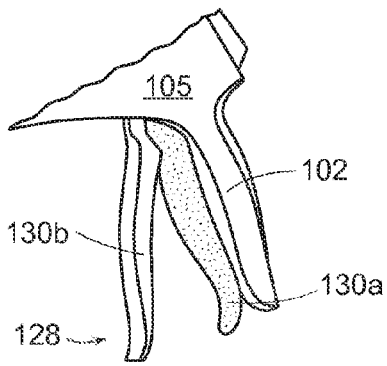
Figure 3E:
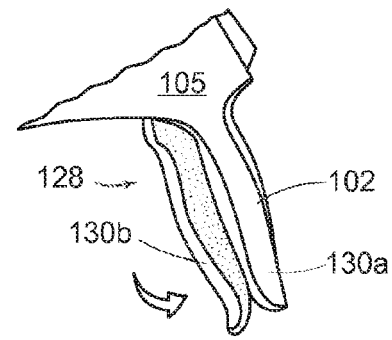
Figure 3F:
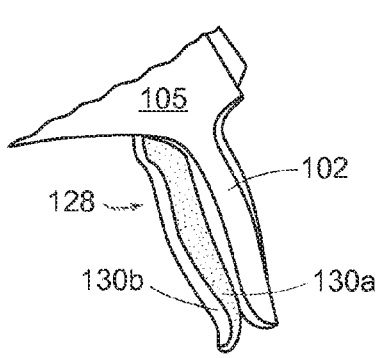

According to certain embodiments, a surgical instrument may comprise, one, a shaft comprising a proximal end and a distal end and, two, a handle extending from the proximal end, wherein the handle comprises a gripping portion and a separable trigger assembly extending from the gripping portion. In various embodiments, as mentioned further above, the separable trigger assembly may comprise a first trigger and a second trigger. In use, the first and second triggers of the trigger assembly may be movable between a first, unactuated position spaced apart from the gripping portion (FIG. 3A) and a second, actuated position adjacent to the gripping portion (FIG. 3B) in order to close the end effector of the surgical instrument. As described in greater detail below, although the second trigger may form part of the first trigger during the first actuation of the trigger assembly, the second trigger may be configured to release from the first trigger when the trigger assembly is in the second, actuated position. In at least one such embodiment, the second trigger may be releasably attached to the first trigger such that after the separable trigger has been moved into its second position, the second trigger can detach from the first trigger and return back to its unactuated condition (FIG. 3C). Such movement of the second trigger can occur independently of the first trigger, as illustrated in FIG. 3D. Thereafter, referring now to FIG. 3E, the second trigger may be movable toward the gripping portion once again to sever the tissue captured within the end effector and/or supply energy to the tissue. In various embodiments, the second trigger can be reconnected to the first trigger to reform the attached trigger assembly in the third actuation position of the trigger assembly 128, as illustrated in FIG. 3F, and returned to its unactuated configuration (FIG. 3A).

The operation of divisible trigger assembly 128 described above can allow the surgical instrument to be operated in two separate stages. More particularly, moving the trigger portions 130a and 130b of the trigger assembly 128 between an unactuated position and their first actuated position can operate the surgical instrument in its first stage while moving the second trigger portion 130b between its second actuated position and its third actuated position can operate the surgical instrument in its second stage. Stated another way, in various embodiments, a first stroke of the trigger portions 130a and 130b together can actuate the first operating stage while a second stroke of the second trigger portion 130b, alone, can actuate the second operating stage. In various circumstances, further to the above, the first operating stage of the surgical instrument can move the jaws of the end effector into a closed configuration while the second operating stage can advance a cutting member relative to the jaws and/or transmit energy to the tissue captured between the jaws, for example. With regard to the exemplary embodiment depicted in FIGS. 4A-7, the first operating stage can advance a cutting member a first, or initial, distance which causes the cutting member to contact the jaws of the end effector and move the jaws into a closed position while the second operating stage can advance the cutting member a second, or final, distance to the distal ends of the jaws, for example. Thus, a first stroke of the trigger assembly 128 can advance the cutting member a first distance to close the jaws while a second stroke of the second portion 130b of the trigger assembly 128 can advance the cutting member a second distance to cut the tissue for example.

As shown in FIGS. 4A-4C, further to the above, the surgical instrument 100 may comprise a gear rack 104 which is operably engaged with the trigger assembly 128 such that the first actuation of the trigger assembly 128 can advance the gear rack 104 a first distance and the second actuation of the trigger assembly 128 can advance the gear rack 104 a second, or subsequent, distance. In various embodiments, as shown in FIG. 4B, the gear rack 104 may comprise a set of gear teeth 103a and a set of ratchet teeth 103b, wherein the trigger assembly 128 can engage the set of gear teeth 103a during the first actuation of the trigger assembly 128 and the set of ratchet teeth 103b during the second actuation of the trigger assembly 128. The translatable member 140 of the surgical instrument 100 may be coupled, or connected, to the gear rack 104 such that the advancement of the gear rack 104 can be transmitted to the translatable member 140. As described in greater detail below, the retraction of the gear rack 104 can also retract the translatable member 140. In various alternative embodiments, the translatable member 140 may comprise the set of gear teeth 103a and the set of ratchet teeth 103b wherein a trigger assembly could directly engage the translatable member in lieu of engaging the intermediate gear rack 104. In any event, in at least one embodiment, the set of gear teeth 103a may be offset from the set of ratchet teeth 103b. As shown in FIG. 4C, the set of gear teeth 103a may be in a different plane than the set of ratchet teeth 103b.

Figure 5:
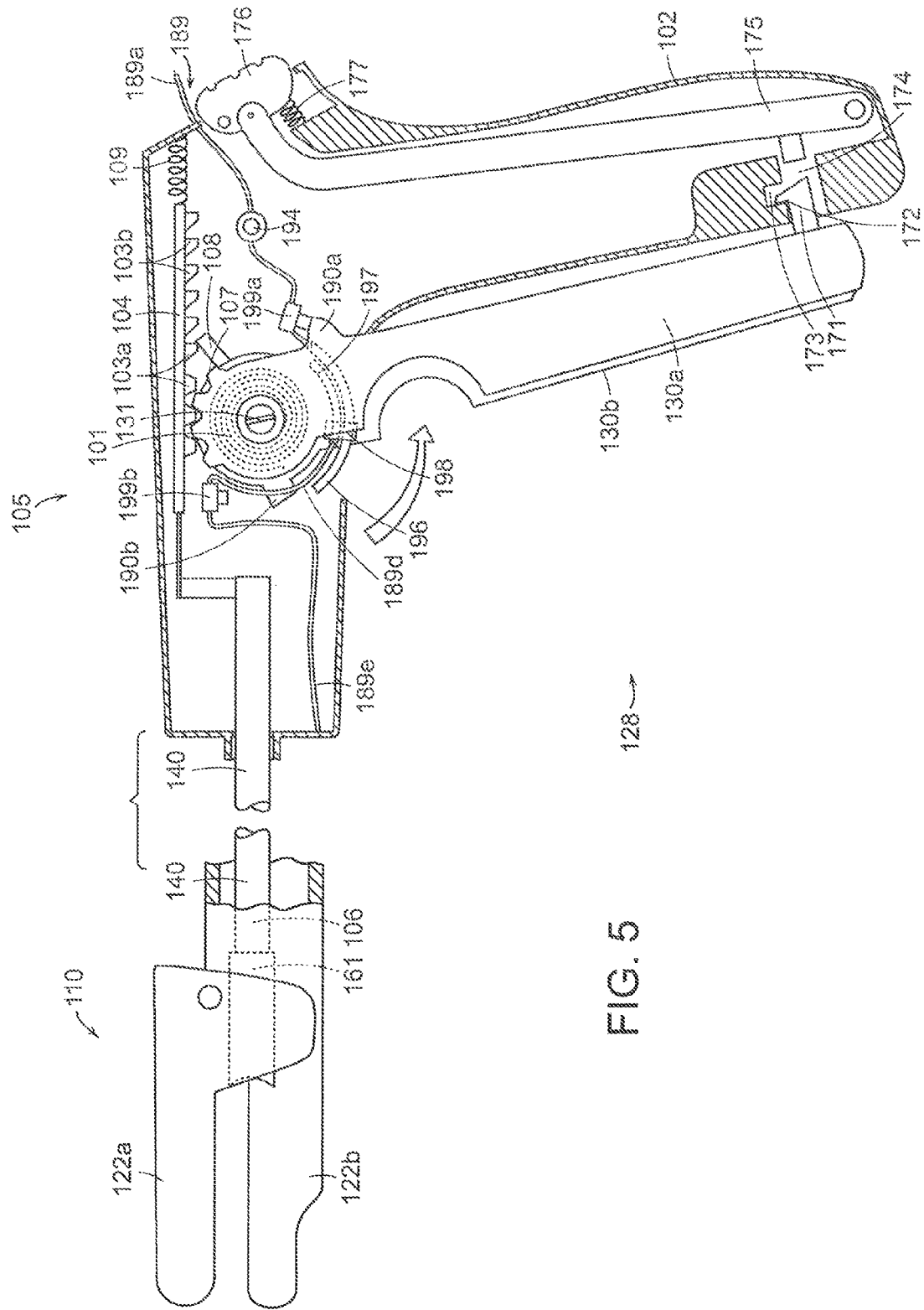
FIG. 5 is a cross-sectional view of the surgical device of FIG. 4A comprising a nested trigger assembly in a first actuated position according to various embodiments.

As shown in FIGS. 4A and 5, the first trigger portion 130a may comprise one or more drive members, such as gear teeth 107, for example, extending therefrom which are configured to engage the set of gear teeth 103a. During the first actuation of the trigger assembly 128, at least one gear tooth 107 may be configured to engage one or more of the gear teeth 103a and drive the rack 104 forward, or distally. Thus, as the first trigger portion 130a and the second portion 130b of the trigger assembly 128 are both moved toward the gripping portion 102 during the first actuation of the trigger assembly 128, as described above, the rack 104 and the translatable member 140 can be advanced distally. As discussed above, the translatable member 140 can close the jaws 122a and 122b when the first trigger portion 130a is moved to the first actuated position. When the trigger assembly 128 has reached its first actuated position (FIG. 5), the jaws 122a and 122b may be in their fully closed configuration. In various embodiment, one or more or the gear teeth 103a may prevent the rack 104 from returning to its unfired position as long as the first trigger portion 130a is held in its second actuated position against the gripping portion 102. As described in greater detail below, the first trigger portion 130a can include a locking mechanism which can be configured to engage the gripping portion 102 and releasably hold the first trigger portion 130a in its second actuated position.

In various embodiments, referring again to FIG. 5, the second trigger portion 130b may comprise at least one drive member, such as pawl 108, for example, extending therefrom which is configured to engage the set of ratchet teeth 103b. The reader will note when comparing FIGS. 4A, 5, and 6 that the set of ratchet teeth 103b may not be aligned with the pawl 108 prior to the first actuation of the trigger assembly 128. Thus, in various embodiments, the first actuation of the trigger assembly 128, and the corresponding initial distal movement of the rack 104, may be required in order to operably align the set of ratchet teeth 103b with the pawl 108 of the second trigger portion 130b. Once the ratchet teeth 103b have been aligned with the pawl 108, the second trigger portion 130b can be actuated a second time, as described above, in order to advance the rack 104, and the translatable member 140 coupled thereto, distally once again. As discussed above, the translatable member 140 can include a cutting member which can incise the tissue captured between the jaws 122a and 122b of the end effector when the second trigger portion 130b is moved between its second actuated position and its third actuated position. When the second trigger portion 130b has reached its third actuated position, the translatable member 140 may be in a fully advanced position. The reader will note that set of gear teeth 103a are free to be advanced distally relative to the first trigger portion 130a after the first trigger portion 130a has been moved into its first actuated position, as described above.

Among other things, the surgical instrument 100 can be configured to, one, manipulate tissue using the jaws 122a and 122b, two, transect the tissue using the knife 161 of translatable member 140 after the tissue has been compressed between the jaws 122a and 122b and, three, seal the tissue using energy supplied to at least one of the jaws 122a and 122b as described in greater detail below. In use, in various circumstances, a surgeon may desire to manipulate the tissue prior to transecting and/or sealing the tissue. In various embodiments, the surgical instrument 100 may be suitable for these purposes as the first actuation of the trigger assembly 128 may only advance the translatable member 140 a sufficient distance to close the jaws 122a and 122b without transecting the tissue captured therein and/or without heating the tissue. Thus, in the event that the surgeon desired to re-open the jaws 122a and 122b and re-position the jaws 122a and 122b relative to the tissue, the surgeon may do so prior to the transection of the tissue and/or prior to the application of energy to the tissue. In certain embodiments, the surgical instrument 100 can include a locking mechanism which holds the first trigger 103a in its first actuated position and, thus, holds the jaws 122a and 122b in their closed configuration. In such embodiments, the surgical instrument 100 can further include a release button, such as release button 176, for example, which can be configured to unlock the first trigger portion 103a and allow the first trigger portion 103a to be returned to its unactuated position. Correspondingly, the return of the first trigger portion 103a to its unactuated position can allow the jaws 122a and 122b to return to their actuated configuration wherein the jaws 122a and 122b can then be repositioned relative to the tissue, as described above. In various embodiments, the surgical instrument 100 can further include at least one return spring, such as trigger spring 101, for example, configured to return the trigger assembly 128 to its unactuated position and at least one spring configured to bias the jaws 122a and 122b into an open configuration after the trigger assembly 128 has been released from its second actuated position.

As outlined above, the surgical instrument 100 can be configured to apply energy to, or direct electrical current through, the tissue captured between the jaws 122a and 122b. In various embodiments, the jaws 122a and 122b can each include one or more electrodes, or conductive surfaces, which can be electrically coupled to the terminals of a power source having different voltage potentials. In various embodiments, the surgical instrument 100 can be configured such that at least one of the electrodes is electrically disconnected from the power source prior to and/or during the first actuation of the trigger assembly 128. In at least one such embodiment, the surgical instrument 100 may comprise a lockout mechanism which is configured to prevent current from flowing from the energy source 145, for example, to at least one of the electrodes, such as, for example, the first electrode 165a and/or second electrode 165b, until the trigger assembly 128 is in the second actuated position and/or moving between the second actuated position and the third actuated position, for example. In at least one such embodiment, the surgical instrument 100 can include a lockout system including a plurality of switches which must be actuated to close an electrical circuit including the first electrode 165a, the tissue, the second electrode 165b, and the energy source 145, for example, and allow the current to flow through the tissue. In the embodiment in which the circuit is closed only when the second trigger portion 103b is being moved from its second actuated position to its third actuated position, for example, the second actuation of the trigger assembly 128 controls the application of energy to the tissue. This embodiment is described in greater detail further below, although other switch arrangements to control the application of energy to the tissue are contemplated and could be used with the surgical instruments described herein.

Referring again to FIG. 4A once again, the reader will note that the second trigger portion 103b of the trigger assembly 128 includes an electrical contact, or connector bar, 198 mounted thereto. In the unactuated position of the trigger assembly 128, illustrated in FIG. 4A, the connector bar 198 is engaged with a first crescent contact 196 mounted to the housing of the surgical instrument handle. In various embodiments, the surgical instrument handle includes the first crescent contact 196 and, in addition, a second crescent contact 197 wherein the crescent contacts 196 and 197 are not in electrical communication with one another except when the connector bar 198 is in contact with both of the first crescent contact 196 and the second crescent contact 197. In various embodiments, the first crescent contact 196 and/or the second crescent contact 197 may each be comprised of a conductive material, such as copper, brass, and/or any other suitable metal, for example. In certain embodiments, the first crescent contact 196 may have a length greater than or equal a length of the second crescent contact 197 such that the connector bar 198 is only in contact with the first crescent contact 196 and not the second crescent contact 197, for example, when the trigger assembly 128 is in certain positions during its stroke. Further to the above, referring to FIG. 4A once again, the connector bar 198 is in contact with the first crescent contact 196 but not the second crescent contact 197 when the trigger assembly 128 is in its unactuated position. In this position, the circuit including the supply conductor 189, the first electrode 165a, the second electrode 165b, and a return conductor is in an open condition as current cannot flow between the first crescent contact 196 and the second crescent contact 197. Thus, when the trigger assembly 128 is in its unactuated position, current cannot flow through the tissue captured between the jaws 122a and 122b. When the trigger assembly 128 is moved toward its first actuated position from its unactuated position, as described above, the bar connector 198 can electrically connect the first crescent contact 196 and the second crescent contact 197. While in some embodiments the connection between the contacts 196 and 197 may be sufficient to close the electrical circuit within the surgical instrument, in other embodiments, however, other switches may need to be closed before current can flow through the circuit as described in greater detail further below.

Figure 6:
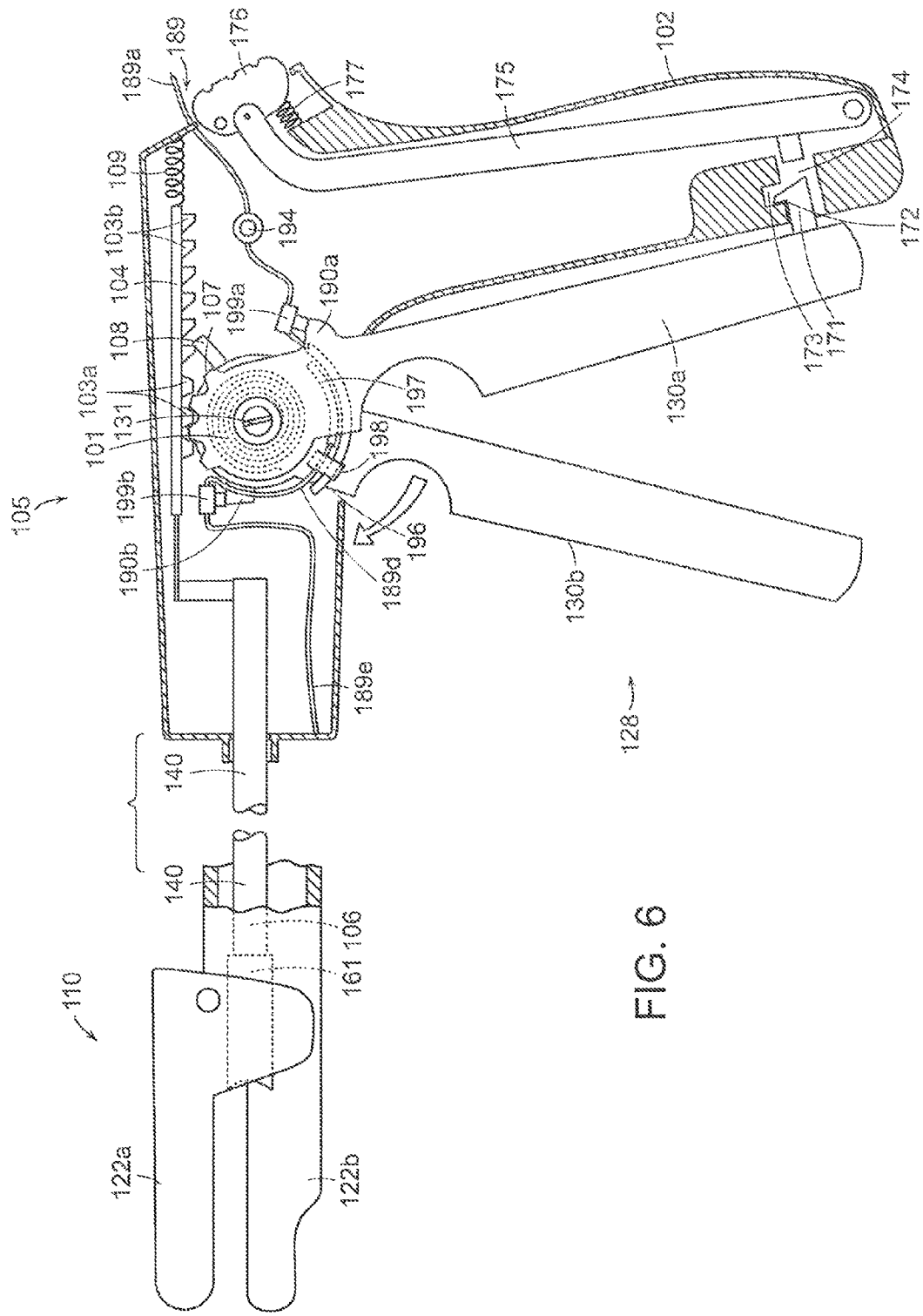
FIG. 6 is a cross-sectional view of the surgical device of FIG. 4A comprising a nested trigger assembly in a second actuated position according to various embodiments.
Figure 7:
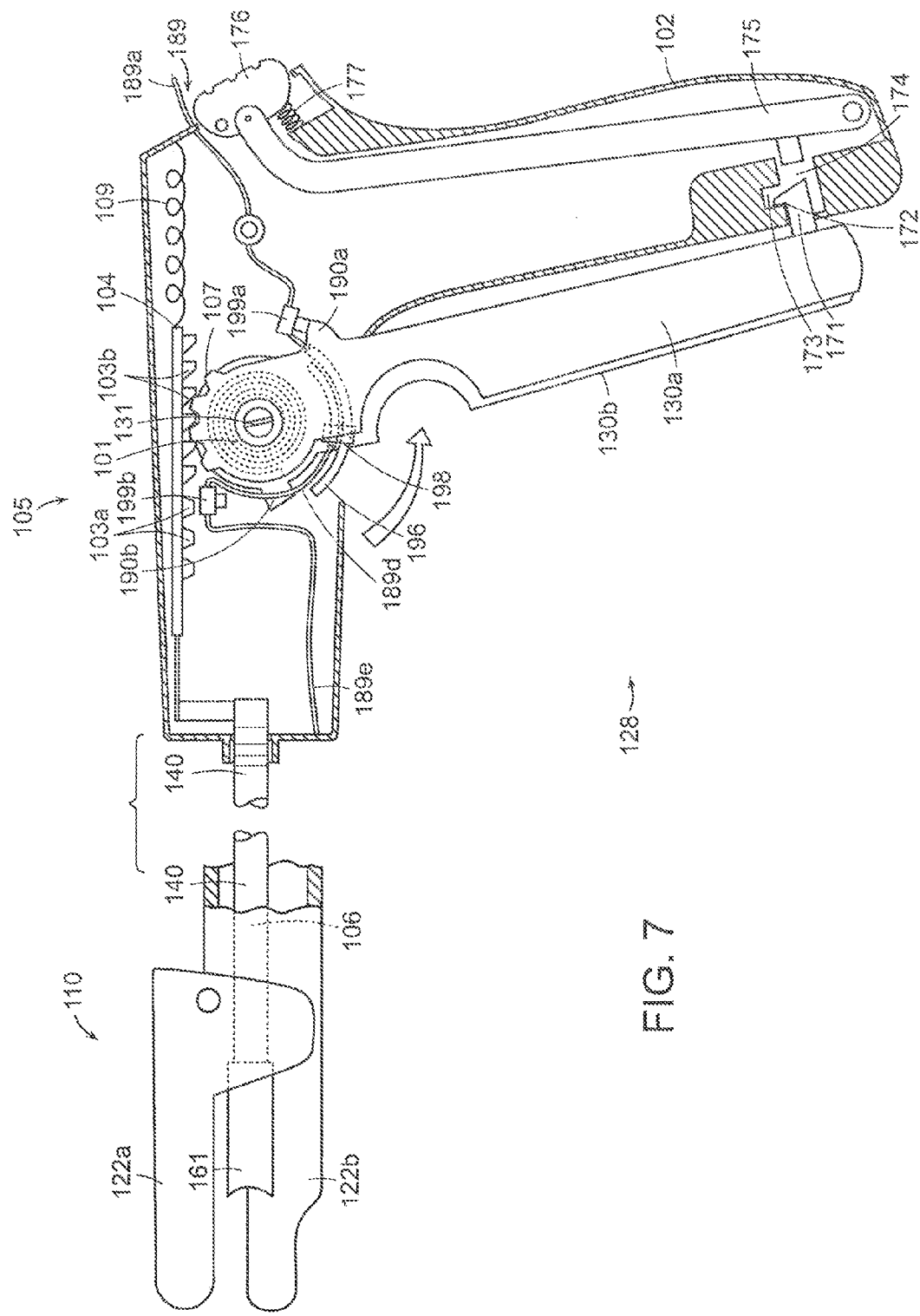
FIG. 7 is a cross-sectional view of the surgical device of FIG. 4A comprising a nested trigger assembly in a third actuated position according to various embodiments.

When the trigger assembly 128 is moved into its first actuated position, referring now to FIG. 5, the first trigger portion 130a can contact and close a first switch 199a. In at least one such embodiment, the first trigger portion 130a can include a tab 190a which can contact the first switch 199a. In this first actuated position of the trigger assembly 128, as the reader will recall, the jaws 122a and 122b have been moved into a closed configuration. In certain embodiments, the closing of the first switch 199a could close the electrical circuit within the surgical instrument 100 thereby allowing current to flow through the tissue captured between the closed jaws 122a and 122b. In such embodiments, the current can flow through the tissue prior to the second stroke of the trigger assembly 128 and prior to the distal advancement of the translatable member 140. In certain other embodiments, other switches may need to be closed subsequent to closing first switch 190a in order to close the electrical circuit within the surgical instrument 100. Referring now to FIG. 6, the first trigger portion 130a can remain in contact with the first switch 199a as the second trigger portion 130b is moved into its second actuated position. When the second trigger portion 140b reaches its second actuated position, a tab 190b extending from the second trigger portion 130b can contact and close a second switch 199b. At this point in the operation of the surgical instrument, the jaws 122a and 122b are in a closed configuration and the first switch 199a and the second switch 199b are in a closed state; however, the connector bar 198 is not in contact with both of the first and second crescent contacts 196 and 197 and, thus, current cannot flow through the circuit to the end effector. Once the second trigger portion 130b is advanced from its second actuated position to its third actuated position as described above, the connector bar 198 can electrically couple the first crescent contact 196 and the second crescent contact 197 and the entire electrical circuit within the surgical instrument 100 can be in a closed configuration thereby allowing current to flow through the tissue.

As described above, and referring to FIG. 4A again, the electrical circuit defined within the surgical instrument 100 can include a supply conductor 198 that can be electrically coupled with an electrode within the first jaw 122a and/or the second jaw 122b. As also described above, a plurality of switches can be present within the supply conductor 189 which may need to be closed in order for current to flow through the supply conductor 189. Thus, the supply conductor 189 can comprise a plurality of conductor segments which electrically connect the switches. For example, the supply conductor 189 can comprise a first segment 189a which electrically couples a cut-off switch 194 with the supply source discussed above. In use, a surgeon can insert the surgical instrument 100 into a patient with the switch 194 in an open condition and close the switch 194 prior to the operation of the surgical instrument 100 described above. Such a cut-off switch can reduce the possibility of inadvertently supplying energy to the end effector. In any event, the supply conductor 189 can further comprise a second segment 189b which can electrically couple the cut-off switch 194 and the first switch 199a and, in addition, a third segment 189c which can electrically couple the first switch 199a and the first crescent contact 196. The supply conductor 189 can further comprise a fourth conductor segment 189d which can electrically couple the second crescent contact 197 and the second switch 199b and, in addition, a fifth conductor segment 189e which can electrically couple the second switch 199b and at least one electrode in the end effector. Thus, when the cut-off switch 194, the first switch 199a, and the second switch 199b are in a closed configuration and the connector bar 198 has closed the connection between crescent contacts 196 and 197, current can flow to the end effector as described above. In such embodiments, the cut-off switch 194, the first switch 199a, the second switch 199b and the crescent contacts 196 and 197 can be in series with one another.

Further to the above, the translatable member 140 can be advanced distally at the same time that energy is being applied to the tissue captured within the end effector, i.e., during the second stroke of the trigger assembly 128. When the second trigger portion 130b has reached its third actuated position, as described above, the circuit can remain closed thereby allowing the surgeon to apply additional energy to the tissue, if so desired. Upon returning the trigger assembly 128 to its unactuated position, the first switch 199a may open thereby interrupting the flow of electrical current through the supply conductor 189. Furthermore, once the trigger assembly 128 has been returned to its unactuated position, the connector bar 198 may no longer connect the first crescent contact 196 to the second crescent contact 197 which would also interrupt the flow of electrical current through the supply conductor 189. In certain embodiments, the surgical instrument 100 can further comprise a trigger return spring operably coupled with the first trigger portion 130a and/or the second trigger portion 130b which can be configured to return the first trigger portion 130a and/or the second trigger portion 130b to their unactuated positions. In at least one such embodiment, the surgical instrument 100 can include a first trigger spring operably coupled with the first trigger portion 130a and a second trigger spring operably coupled to the second trigger portion 130b wherein the first and second trigger springs can be configured to return the first and second trigger portions 130a and 130b independently of one another and/or at the same time. In various embodiments, the surgical instrument 100 can comprise at least one biasing spring, such as spring 109, for example, having a first end mounted to the handle housing and a second end mounted to the gear rack 104 which can be configured to pull the gear rack 104 proximally toward its unfired position.

Further to the above, the first and second trigger portions 130a and 130b can advance the gear rack 104 distally and, as the trigger portions 130a and 130b are being returned to their unactuated positions, the spring 109 can bias the rack 104 back to its unactuated position. In at least one such embodiment, the pawl 108 can slide relative to the ratchet teeth 103b and the gear teeth 103a can remesh and reset relative to the gear teeth 107 extending from the first trigger portion 130a. At such point, the surgical instrument 100 can be reused once again to capture tissue between the jaws 122a and 122b, apply energy to the tissue, and/or transect the tissue, as outlined above.

As mentioned above, the handle 105 may comprise a locking mechanism configured to retain the first trigger portion 130a in its first actuated position. For example, the first trigger portion 130a can comprise a lock 170 extending therefrom which can comprise a cantilever arm 171 and a latching, or locking surface, 172 which can be configured to enter a lock cavity 174 defined in the gripping portion 102 when the first trigger portion 103a is moved into its first actuated position. In at least one such embodiment, the locking surface 172 can move behind a lock surface 173 defined in the lock cavity 174. In order to unlock the first trigger portion 130a, the surgical instrument 100 can further comprise an actuator 176 which can be depressed to push the lock 170 out of the lock cavity 174. More particularly, the actuator 176 can be operably connected to a lever arm 175 which can be rotated or pivoted to contact the lock 170 when the actuator 176 is depressed. Once the actuator 176 is released by the surgeon, a return spring 177 can reposition and reset the actuator 176 and the lever arm 175.

In various embodiments, the trigger assembly 128 may comprise a release mechanism movable between a first position in which it is engaged with the second trigger portion 130b and a second position in which it is disengaged from the second trigger portion 130b. The release mechanism may be in the first position when the portion of the trigger assembly 128 is in the unactuated position and when the trigger assembly 128 is moved between its unactuated position and its first actuated position. The release mechanism can be moved from its first position to its second position to uncouple the second trigger portion 130b from the first trigger portion 130a. Thus, in various embodiments, the release mechanism can hold the first trigger portion 130a and the second trigger portion 130b together during the first actuation of the trigger assembly and release the second trigger portion 130b after the first actuation such that the second trigger portion 130b can be actuated once again as described above.

Figure 8A:
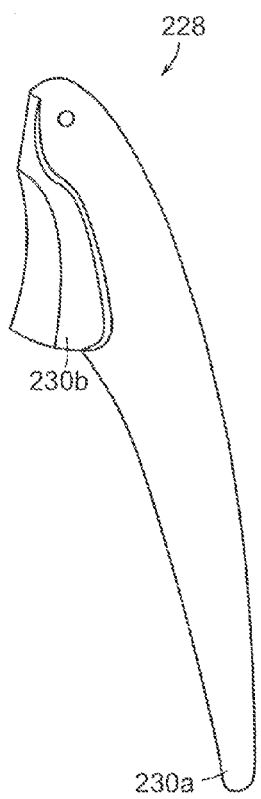
FIGS. 8A and 8B are perspective views of a nested trigger assembly for a surgical instrument according to various embodiments.
Figure 8B:
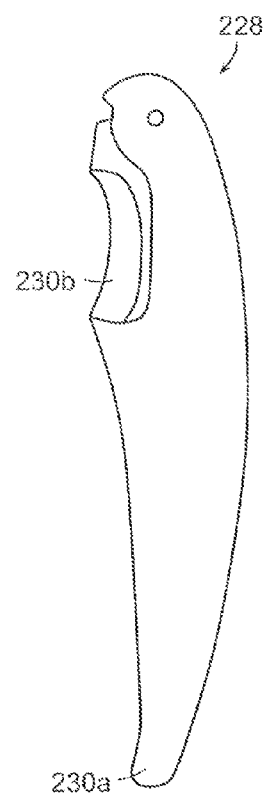

Referring to FIGS. 8A and 8B, according to certain embodiments, a separable trigger assembly 228 for a surgical instrument may generally comprise a first trigger 230a and a second trigger 230b. The first trigger 230a and second trigger 230b may be movable together on a first stroke of the separable trigger assembly, such as, for example, from an unactuated position to a first actuated position. The second trigger 230b may form a portion of the first trigger 230a prior to the first stroke. The second trigger 230b may form a portion of the first trigger 230a prior to and during the first stroke. In at least one embodiment, the second trigger 230b may be releasably attached to the first trigger 230a after the first stroke. The second trigger 230b may not form a portion of the first trigger 230a after the first stroke. The second trigger 230b may be configured to be biased away from the first trigger 230a after the first stroke and before a second stroke. The second trigger 230b may be configured to be moved toward to the first trigger 230a during the second stroke, such as, for example, from a second actuated position to a third actuated position. The second trigger 230b may form a portion of the first trigger 230a after the second stroke.

In various embodiments, the separable trigger assembly 228 may comprise a release mechanism movable between an engaged position in which it contacts the second trigger 230b and a disengaged position in which it is free from contact with the second trigger 230b. The release mechanism may be in the engaged position prior to and during the first stroke and after the second stroke.

In various embodiments, the surgical instrument may comprise a switch that may be actuated to supply current to the electrodes positioned within the end effector. The surgical instrument may comprise a switch that may be tripped to supply current to the electrodes positioned within the end effector when the trigger assembly is moved into the third actuated position. In at least one embodiment, the switch may be in an open configuration as the trigger assembly is moved through the range of motion from the unactuated position to the third actuated position, and once tripped by the trigger assembly, such as, for example, when the second trigger is in the third actuated position, the switch may be in a closed configuration as the trigger assembly is moved through from the third actuated position to the unactuated position. In various embodiments, current may not flow through the electrodes in the end effector as the trigger assembly is moved from the unactuated position to the first actuated position and as the first jaw is being moved into its closed position.

In various embodiments, current may flow through the electrodes as the trigger assembly is moved from the first actuated position to the third actuated position. In various embodiments, current may flow through the electrodes as the trigger assembly is moved from the second actuated position to the third actuated position and as the knife edge is being advanced distally by the trigger assembly as described above. In various embodiments, the switch may be positioned within handle such that the switch is aligned with the trigger assembly when the trigger assembly is in the third actuated position.

Referring to FIG. 1, the surgical instrument 100 comprising an electrical source 145 and a controller 150, for example, may be configured to provide different electrosurgical energy-delivery operating modes which, in certain embodiments, may depend on the amount, or degree, of jaw closure. In any event, in various circumstances, further to the above, the degree of jaw closure may be represented by the degree of actuation of the trigger assembly 128, such as, for example, the first trigger portion 130a, toward the gripping portion 102 and/or the axial translation of translational member 140. In various circumstances, it may be useful to switch between different electrosurgical energy-delivery operating modes depending on the volume of tissue captured within the end effector 110 of the surgical instrument 100 and the amount of compression applied to the tissue. For example, the surgical instrument 100 may deliver Rf energy in a first operating mode to large volumes of the captured tissue in order to cause an initial dehydration of the tissue, wherein the surgical instrument 100 may thereafter switch, and/or be switched by controller 150, for example, to a second operating mode which allows for more effective tissue welding. In various circumstances, this second operating mode may provide a greater amount or a lesser amount of energy to the tissue and/or adjust the manner or location in which the energy is being supplied to the tissue. Alternatively, when engaging a lesser volume of tissue, for example, the surgical instrument 100 and/or accompanying system may deliver Rf energy in only one operating mode which can be best suited for tissue welding, for example.

In various embodiments, surgical instrument 100 and/or accompanying system may comprise a control system and/or controller 150 to switch the surgical instrument 100 from one operating mode to another mode after the jaws 122a and 122b have been closed a predetermined amount. In various embodiments, the switchover may occur at 10%, 20%, 30%, 40%, 50%, 60%, 70%, and/or 80% of the jaw closure, for example. In certain embodiments, the surgical instrument 100 may comprise a sensor (not shown) configured to detect the degree to which the jaws 122a and 122b have been closed. In various embodiments, the switching between electrosurgical modes may be triggered by one or more operational parameters, such as (i) the degree of jaw closure as described above, (ii) the impedance of the engaged tissue, and/or (iii) the rate of change of impedance or any combination thereof. Furthermore, the polarity of the electrodes may be switched more than two times during the operation of the surgical instrument. Other operating modes are disclosed in U.S. patent application Ser. No. 12/050,462, entitled ELECTROSURGICAL INSTRUMENT AND METHOD, filed on Mar. 18, 2008, the entire disclosure of which is incorporated by reference herein.

In various embodiments, as described above, current may flow from one electrode to another while passing through the tissue captured by the end effector of the surgical instrument. As also described above, the current passing through the tissue may heat the tissue. In various circumstances, however, the tissue may become overheated. In order to avoid such overheating, the electrodes of various surgical instruments may comprise materials which may no longer conduct current, or may conduct at least substantially less current, when the electrode materials have reached or exceeded a certain temperature. Stated another way, in at least one embodiment, the electrical resistance of the electrode material may increase with the temperature of the material and, in certain embodiments, the electrical resistance of the material may increase significantly when the material has reached or exceeded a certain transition, or switching, temperature. In various circumstances, such materials may be referred to as positive temperature coefficient, or PTC, materials. In at least some such PTC materials, the PTC material may be comprised of a first non-conductive material, or substrate, which has a high electrical resistance and, in addition, a second, conductive material, or particles, having a lower electrical resistance interdispersed throughout the substrate material. In at least one embodiment, the substrate material may comprise polyethylene and/or high-density polyethylene (HDPE), for example, and the conductive material may comprise carbon particles, for example. In any event, when the temperature of the PTC material is below its transition temperature, the conductive material may be present in the non-conductive material in a sufficient volumetric density such that the current may flow through the PTC material via the conductive particles. When the temperature of the PTC material has exceeded its transition temperature, the substrate, or non-conductive material may have sufficiently expanded and/or changed states such that the conductive particles are no longer sufficiently in contact with one another in order provide a sufficient path for the current to flow therethrough. Stated another way, the expansion and/or state change of the substrate material may cause the volumetric density of the conductive particles to fall below a sufficient volumetric density in order for current to be conducted therethrough, or at least substantially conducted therethrough. In various circumstances, as a result of the above, the PTC material may act as a circuit breaker which can prevent, or at least inhibit, additional energy from reaching the tissue being treated, that is, at least until the PTC material has cooled sufficiently and reached a temperature which is below the transition, or switching, temperature. At such point, the PTC material could begin to conduct current again.

Further to the above, describing a material as having a positive temperature coefficient of resistance (PTC) may mean that the resistance of the material increases as the temperature of the material increases. Many metal-like materials exhibit electrical conduction that has a slight positive temperature coefficient of resistance. In such metal-like materials, the PTC's variable resistance effect may be characterized by a gradual increase in resistance that is linearly proportional to temperature, i.e., a linear PTC effect. A "nonlinear" PTC effect may be exhibited by certain types of polymer matrices, or substrates, which are doped with conductive particles. These polymer PTC compositions may comprise a base polymer that undergoes a phase change or can comprise a glass transition temperature $T_g$ such that the PTC composition may have a resistance that increases sharply over a narrow temperature range.

Polymeric PTC material may consist of a crystalline or semi-crystalline polymer (e.g., polyethylene) that carries a dispersed filler of conductive particles, such as carbon powder or nickel particles, for example, therein. In use, a polymeric PTC material may exhibit temperature-induced changes in the base polymer in order to alter the electrical resistance of the polymer-particle composite. In a low temperature state, the crystalline structure of the base polymer may cause dense packing of the conductive particles (i.e., carbon) into its crystalline boundaries so that the particles may be in close proximity and allow current to flow through the PTC material via these carbon "chains". When the PTC material is at a low temperature, numerous carbon chains may form the conductive paths through the material. When the PTC material is heated to a selected level, or an over-current causes $I^2R$ heating (Joule heating) within the PTC material, the polymer base material may be elevated in temperature until it exceeds a phase transformation temperature. As the polymer passes through this phase transformation temperature, the crystalline structure may change to an amorphous state. The amorphous state may cause the conductive particles to move apart from each other until the carbon chains are disrupted and can no longer conduct current. Thus, the resistance of the PTC material increases sharply. In general, the temperature at which the base polymer transitions to its amorphous state and affects conductivity is called its switching temperature $T_s$. In at least one embodiment, the transition or switching temperature $T_s$ may be approximately 120 degrees Celsius, for example. In any event, as long as the base polymer of the PTC material stays above its switching temperature Ts, whether from external heating or from an overcurrent, the high resistance state will remain. Reversing the phase transformation allows the conductive particle chains to reform as the polymer re-crystallizes to thereby restore multiple current paths, and a low resistance, through the PTC material. Conductive polymer PTC compositions and their use are disclosed in U.S. Pat. Nos. 4,237,441; 4,304,987; 4,545,926; 4,849,133; 4,910,389; 5,106,538; and 5,880,668, the entire disclosures of which are incorporated by reference herein.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
  an end effector, comprising:
    a law movable between an open position and a closed position;
    a cutting element configured to move through the end effector; and
    an electrode;
  a drive system, comprising:
    a closure drive portion; and
    a firing drive portion;
  a handle comprising a separable trigger assembly, the separable trigger assembly comprising:
    a first trigger configured to engage the closure drive portion during a first stroke of the separable trigger assembly, wherein the first stroke is configured to move the law from the open position to the closed position;
    a second trigger, wherein the first trigger and the second trigger are movable together on the first stroke of the separable trigger assembly, wherein the second trigger is disengaged from the firing drive portion during the first stroke, wherein the second trigger is configured to be biased away from the first trigger after the first stroke and before a second stroke, wherein the second trigger is configured to be moved toward the first trigger during the second stroke, wherein the second trigger is configured to engage the firing drive portion during the second stroke, and wherein the second stroke is configured to move the cutting element through the end effector; and
    a releasable lock configured to engage and restrain the first trigger when the second trigger moves away from the first trigger after the first stroke such that the jaw of the end effector remains in the closed position; and
  an energy lockout configured to prevent current from flowing to the electrode until the second trigger moves away from the first trigger after the first stroke.

2. The separable trigger assembly of claim 1, wherein the second trigger forms a portion of the first trigger prior to the first stroke and after the second stroke.

3. The separable trigger assembly of claim 1, wherein the second trigger forms a portion of the first trigger prior to and during the first stroke and after the second stroke.

4. The surgical instrument of claim 1, wherein the handle further comprises:
  a gripping portion; and
  a spring configured to bias the first trigger and the second trigger away from the gripping portion.

5. The surgical instrument of claim 4, wherein the releasable lock is configured to resist the spring to restrain the first trigger when the second trigger moves away from the first trigger.

6. The surgical instrument of claim 1, wherein the first trigger is nested at least partially within the second trigger during the first stroke.

7. The surgical instrument of claim 1, wherein the first trigger is nested at least partially within the second trigger after the second stroke.

8. The surgical instrument of claim 1, wherein the jaw further comprises a positive temperature coefficient body portion.

9. A surgical instrument, comprising:
  an end effector, comprising:
    a jaw movable between an open position and a closed position;
    a cutting element configured to move relative to the jaw; and
    an electrode;
  a drive system, comprising:
    a closure drive portion; and
    a firing drive portion;
  a handle comprising a separable trigger assembly, wherein the separable trigger assembly comprises:
    a closure trigger configured to engage the closure drive portion during a first stroke of the separable trigger assembly, wherein the first stroke is configured to move the jaw from the open position to the closed position, and wherein the closure trigger is configured to move in a first direction during the first stroke; and
    a firing trigger movable with the closure trigger in the first direction during the first stroke, wherein the firing trigger is disengaged from the firing drive portion during the first stroke, wherein the firing trigger is configured to be moved in a second direction after the first stroke and before a second stroke, and wherein the firing trigger is configured to move into engagement with the firing drive portion after the first stroke and before the second stroke; and
  an energy lockout configured to prevent current from flowing to the electrode until the firing trigger moves in the second direction after the first stroke.

10. The surgical instrument of claim 9, further comprising a releasable lock configured to engage and restrain the closure trigger when the firing trigger moves in the second direction after the first stroke such that the jaw of the end effector remains in the closed position.

11. The surgical instrument of claim 10, wherein the handle further comprises:
  a gripping portion; and
  a spring configured to bias the closure trigger and the firing trigger away from the gripping portion.

12. The surgical instrument of claim 11, wherein the releasable lock is configured to resist the spring to restrain the closure trigger when the firing trigger moves away from the closure trigger.

13. The surgical instrument of claim 9, wherein the closure trigger is nested at least partially within the firing trigger during the first stroke.

14. The surgical instrument of claim 9, wherein the closure trigger is nested at least partially within the firing trigger after the second stroke.

15. The surgical instrument of claim 9, wherein the jaw further comprises a positive temperature coefficient body portion.

16. A surgical instrument, comprising:
- an end effector, comprising:
  - a jaw movable between an open position and a closed position;
  - a cutting element configured to move relative to the jaw; and
  - an electrode;
- a drive system, comprising:
  - a closure drive portion; and
  - a firing drive portion;
- a handle comprising a trigger assembly, wherein the trigger assembly comprises:
  - a closure trigger; and
  - a firing trigger, wherein the closure trigger and the firing trigger are movable as a unit during a first actuation of the trigger assembly, wherein the closure trigger is engaged with the closure drive portion and the firing trigger is disengaged with the firing drive portion during the first actuation of the trigger assembly;
  - wherein the closure trigger is configured to be restrained and the firing trigger is configured to be reset after the first actuation of the trigger assembly; and
  - wherein the firing trigger is engaged with the firing drive portion during a second actuation of the trigger assembly;
- means for preventing current from flowing to the electrode until the firing trigger has been reset.

17. The surgical instrument of claim 16, further comprising restraining means for engaging and restraining the closure trigger when the firing trigger is being reset.

18. The surgical instrument of claim 16, wherein the handle further comprises:
- a gripping portion; and
- a spring configured to bias the closure trigger and the firing trigger away from the gripping portion.

19. The surgical instrument of claim 16, wherein the closure trigger is nested at least partially within the firing trigger during the first actuation of the trigger assembly.

20. The surgical instrument of claim 16, wherein the closure trigger is nested at least partially within the firing trigger after the second actuation of the trigger assembly.

* * * * *